United States Patent [19]

Freeman

[11] Patent Number: 5,704,388
[45] Date of Patent: Jan. 6, 1998

[54] TUBULAR TOOTHPICK HAVING A FEATHERED TIP

[76] Inventor: Roger Freeman, 8353 Somerset Dr., Prairie Village, Kans. 66207

[21] Appl. No.: 721,803

[22] Filed: Sep. 27, 1996

[51] Int. Cl.⁶ ................................................. A01C 51/00
[52] U.S. Cl. ......................................................... 132/329
[58] Field of Search ......................... 132/321, 329; 433/141, 142, 143

[56] References Cited

U.S. PATENT DOCUMENTS

| | | |
|---|---|---|
| 194,447 | 8/1877 | Laurence . |
| 195,664 | 9/1877 | Smith . |
| 469,064 | 2/1892 | McKay . |
| 516,409 | 3/1894 | Southwell . |
| 656,476 | 8/1900 | Schellenbach . |
| 1,527,028 | 2/1925 | Daniel . |
| 1,527,845 | 2/1925 | Daniel . |

*Primary Examiner*—Todd E. Manahan
*Attorney, Agent, or Firm*—Hovey, Williams, Timmons & Collins

[57] ABSTRACT

A tubular toothpick (10) that can be used to remove food particles from between a user's teeth, gums and periodontal pockets without damaging the soft tissue of the user's gums is disclosed. The toothpick (10) is formed from synthetic resin materials and includes an elongated tubular body (12) presenting a longitudinal axis and a pair of axially opposed ends (14,16). One of the ends (14) includes an oblique leading surface (18) defining a cleaning edge. A plurality of slits (22) are formed in the cleaning edge that define therebetween a plurality of spaced-apart and independently movable finger portions (23). The independently moveable finger portions (23) feather and soften the cleaning edge of the toothpick for permitting the toothpick to be inserted between a user's teeth and gums without damaging the soft tissue of the user's gums.

7 Claims, 1 Drawing Sheet

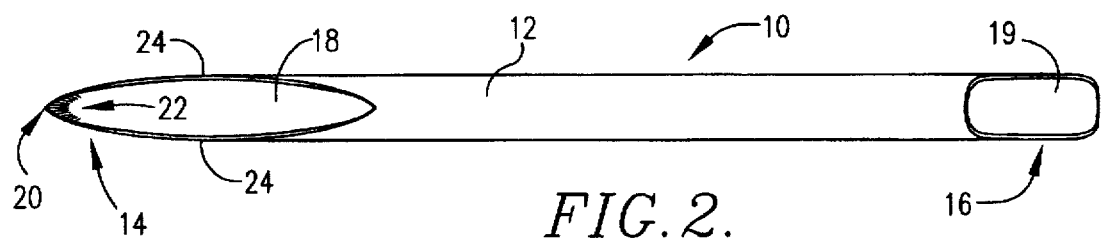
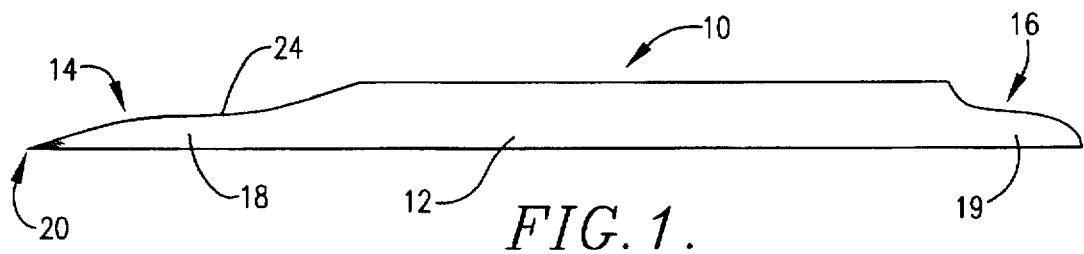
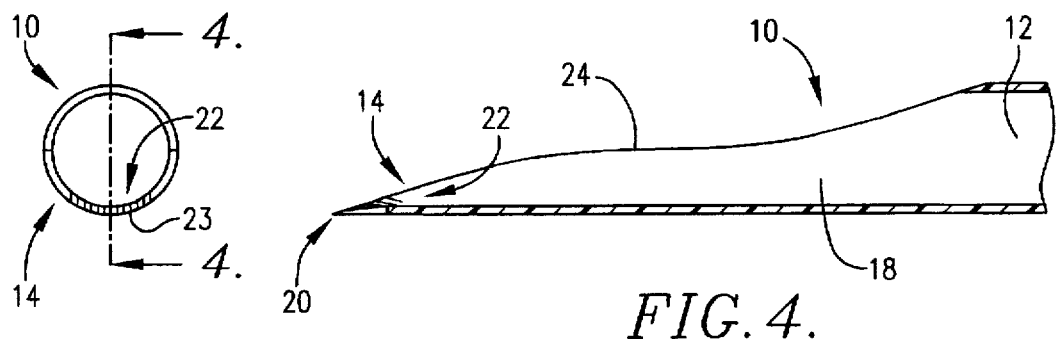
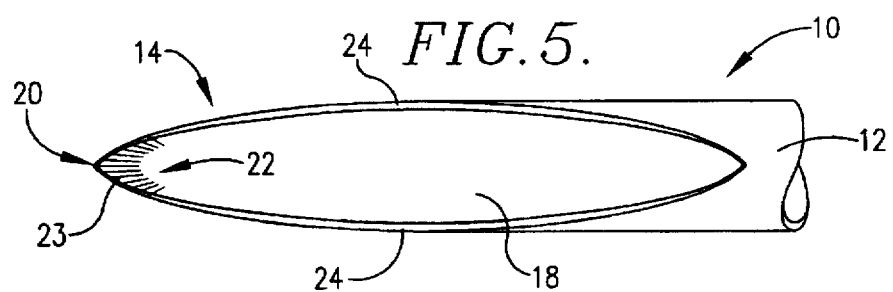
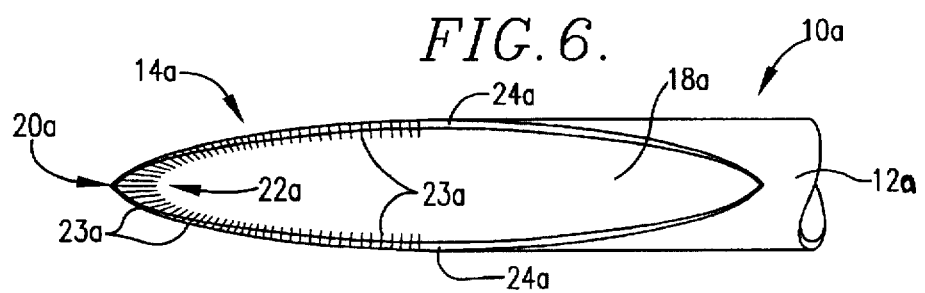

5,704,388

1

TUBULAR TOOTHPICK HAVING A FEATHERED TIP

BACKGROUND OF THE INVENTION

1. Field of the Invention

The present invention relates to toothpicks. More particularly, the invention relates to a tubular toothpick formed from synthetic resin materials and having an oblique leading surface defining a cleaning edge. A plurality of slits are formed in the oblique leading surface and define therebetween a plurality of spaced-apart and independently movable finger portions. The finger portions feather the cleaning edge of the toothpick and flex when the toothpick is inserted between a user's teeth and gums for preventing damage to the soft tissue of the user's gums.

2. Description of the Prior Art

Toothpicks are commonly used to remove food particles and other foreign matter from between user's teeth and gums. Known toothpicks are typically formed from either wood or plastic.

Unfortunately, wooden toothpicks have a short operational life because they easily shred and break when they are forced between users' teeth. They are also ineffective at reaching the interior area between teeth such as periodontal pockets because the steep tapering of the toothpick allows only the outermost portion of the tips of the toothpicks to penetrate between users' teeth.

Plastic toothpicks have a longer operational life than wooden toothpicks because they are relatively stronger than wooden toothpicks. However, plastic toothpicks often cause damage to the soft tissue of users' gums when the toothpicks are forced between the users' teeth and gums because of the increased rigidity and strength of the toothpicks. Thus, many manufacturers have discontinued making plastic toothpicks and have returned to wooden toothpicks despite their short operational life.

Accordingly, there is a need for an improved toothpick that benefits from the longer operational life of plastic materials, that has a uniform wall thickness which permits a greater portion of the toothpick to penetrate between a user's teeth, and that does not cause damage to the soft tissue of a user's gums when the toothpick is forced between the user's teeth and gums.

SUMMARY OF THE INVENTION

The present invention solves the above-described problems and provides a distinct advance in the art of toothpick design. More particularly, the present invention provides a toothpick that is formed from synthetic resin materials and therefore has a longer operational life than wooden toothpicks. The toothpick has a uniform wall thickness so that a greater portion of the toothpick can penetrate between a user's teeth. Moreover, the toothpick includes structure for preventing the toothpick from damaging the soft tissue of a user's gums when the toothpick is used to remove food particles from periodontal pockets and between the user's teeth and gums.

The toothpick of the present invention broadly includes an elongated tubular body presenting a longitudinal axis and a pair of axially opposed ends. One of the ends includes a tapered oblique leading surface defining a tooth and gum cleaning edge.

A plurality of slits are formed in the cleaning edge of the oblique leading surface for feathering the edge. The slits define therebetween a plurality of spaced-apart and independently movable finger portions. The independently moveable finger portions feather and soften the cleaning edge of the toothpick and flex when the toothpick is inserted between a user's teeth and gums for preventing damage to the soft tissue of the user's gums.

Accordingly, the toothpick of the present invention is much safer to use than prior art toothpicks. Additionally, since the toothpick is formed from synthetic resin materials rather than wood, it has a long operational life.

BRIEF DESCRIPTION OF THE DRAWING FIGURES

A preferred embodiment of the present invention is described in detail below with reference to the attached drawing figures, wherein:

FIG. 1 is a side elevational view of a toothpick constructed in accordance with a first preferred embodiment of the invention;

FIG. 2 is a plan view of the toothpick of FIG. 1;

FIG. 3 is a front elevational view of the toothpick of FIG. 1;

FIG. 4 is a partial section view of the toothpick taken along line 4—4 of FIG. 3;

FIG. 5 is a partial plan view of the cleaning edge of the toothpick illustrated in FIG. 1; and FIG. 6 is a partial plan view of the cleaning edge of a toothpick constructed in accordance with a second preferred embodiment of the invention.

DETAILED DESCRIPTION OF THE PREFERRED EMBODIMENTS

Turning now to the drawing figures, and particularly FIG. 1, a toothpick 10 constructed in accordance with a first preferred embodiment of the invention is illustrated. The toothpick 10 is provided for cleaning food particles and other foreign matter from between a user's teeth, gums and periodontal pockets and broadly includes an elongated tubular body 12 presenting a longitudinal axis and a pair of axially opposed ends 14,16.

In more detail, the tubular body 12 is preferably formed from synthetic resin materials such as polyethylene or polypropolene and presents a uniform wall thickness. In preferred forms, the toothpick presents an outside diameter of approximately 1/16–1/4" and a wall thickness of approximately 0.004–0.010". These dimensions allow the entire the toothpick to penetrate between a user's teeth.

The overall length of the toothpick 10 is preferably approximately 2"–3". Those skilled in the art will appreciate that the toothpick 10 may be formed from other suitable materials and may be of any desired size.

The end 14 of the toothpick 10 includes a tapered edge 24 that defines an oblique leading surface 18 terminating in a generally sharp point 20. As best illustrated in FIGS. 1 and 2, the tapered edge 24 is preferably circular in plan view and concavo-convex or serpentine shaped in side view.

The oblique leading surface 18 defines a tooth and gum cleaning edge that can be inserted between a user's teeth and gums to remove food particles therefrom. In preferred forms, the oblique leading surface 18 is approximately 5/8" long.

The second end 16 of the toothpick 10 may also include a tapered oblique leading surface 19 that facilitates griping of the toothpick.

As best illustrated in FIG. 5, the oblique leading surface 18 of the end 14 includes a plurality of elongated and spaced-apart slits 22 formed therein for feathering the tip 20 and the cleaning edge of the toothpick 10. The slits 22 are preferably approximately 1/16"–1/4" in length and spaced approximately 1/10"–1/3" apart.

The slits 22 define therebetween a plurality of spaced-apart and independently movable finger portions 23. The finger portions 23 flex when the cleaning edge of the toothpick is inserted between a user's teeth and gums for softening the cleaning edge. This permits the toothpick 10 to be inserted between a user's teeth and gums without damaging the soft tissue of the user's gums.

In the first embodiment of the invention, the slits 22 are formed only near the tip 20 of the oblique leading surface 18 and extend rearwardly from the tip. The slits 22 at the tip 20 extend generally parallel to the longitudinal axis of the tubular body 12 and the slits spaced from the tip extend at a angle relative to the longitudinal axis as illustrated in FIG. 5.

In a second embodiment of the invention illustrated in FIG. 6, the slits 22a are formed both across the tip 20a and the sides of the tapered edge 24a of the oblique leading surface 18a. The longitudinal axes of some of the slits and finger portions extend at an angle relative to the longitudinal axis of the tubular body. This permits the sides of the oblique leading surface 18 as well as the tip 20 to be used for cleaning the user's teeth and gums.

In a third embodiment of the invention, the oblique leading surface of the toothpick does not include slits or moveable fingers. Instead, the thickness of the oblique leading surface is tapered so that the tip and approximately ½ the length of the oblique leading surface is more flexible than the remaining portion of the toothpick. This permits the tip and the leading half of the oblique leading surface to be inserted between a user's teeth and gums without damaging the soft tissue of the gums.

Although the invention has been described with reference to the preferred embodiment illustrated in the attached drawing figures, it is noted that equivalents may be employed and substitutions made herein without departing from the scope of the invention as recited in the claims.

Having thus described the preferred embodiment of the invention, what is claimed as new and desired to be protected by Letters Patent includes the following:

1. A toothpick comprising:

an elongated tubular body presenting a longitudinal axis and a pair of axially opposed ends, one of said ends including a tapered oblique leading surface defining a tooth and gum cleaning edge, said cleaning edge of said oblique leading surface including a plurality of spaced-apart slits formed therein defining therebetween a plurality of independently moveable finger portions for feathering said cleaning edge, wherein some of said slits and said finger portions extend generally parallel to the longitudinal axis of said tubular body and some of said slits and finger portions extend at an angle relative to the longitudinal axis of said tubular body.

2. The toothpick as set forth in claim 1, said tubular body presenting an outside diameter of approximately 1/16–1/4" and a wall thickness of approximately 0.004–0.010".

3. The toothpick as set forth in claim 1, wherein said tubular body is formed of synthetic resin materials.

4. The toothpick as set forth in claim 1, wherein said slits are approximately 1/16"–1/4" in length.

5. A toothpick comprising:

an elongated tubular body formed of synthetic resin materials and presenting a longitudinal axis and a pair of axially opposed ends, one of said ends including a tapered oblique leading surface defining a tooth and gum cleaning edge, the other of said ends also including a tapered oblique leading surface defining a gripping surface, said cleaning edge of said oblique leading surface including a plurality of spaced-apart slits formed therein defining therebetween a plurality of independently moveable finger portions for feathering said cleaning edge, wherein some of said slits and said finger portions extend generally parallel to the longitudinal axis of said tubular body and some of said slits and finger portions extend at an angle relative to the longitudinal axis of said tubular body.

6. The toothpick as set forth in claim 5, said tubular body presenting an outside diameter of approximately 1/16–1/4" and a wall thickness of approximately 0.004–0.010".

7. The toothpick as set forth in claim 5, wherein said slits are approximately 1/16"–1/4" in length.

* * * * *